US010264955B2

(12) United States Patent
Saito

(10) Patent No.: US 10,264,955 B2
(45) Date of Patent: Apr. 23, 2019

(54) PROCESSOR DEVICE AND METHOD FOR OPERATING SAME, AND ENDOSCOPIC SYSTEM AND METHOD FOR OPERATING SAME

(71) Applicant: FUJIFILM Corporation, Tokyo (JP)

(72) Inventor: Takaaki Saito, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/720,448

(22) Filed: Sep. 29, 2017

(65) Prior Publication Data

US 2018/0020903 A1 Jan. 25, 2018

Related U.S. Application Data

(63) Continuation-in-part of application No. PCT/JP2016/057484, filed on Mar. 10, 2016.

(30) Foreign Application Priority Data

Apr. 2, 2015 (JP) .................................. 2015-075888
Jan. 15, 2016 (JP) .................................. 2016-005911

(51) Int. Cl.
G06K 9/00 (2006.01)
A61B 1/04 (2006.01)
(Continued)

(52) U.S. Cl.
CPC ............ *A61B 1/04* (2013.01); *A61B 1/00009* (2013.01); *A61B 5/1459* (2013.01);
(Continued)

(58) Field of Classification Search
CPC ..... A61B 1/04; A61B 1/00009; A61B 1/0638; A61B 5/14551; A61B 5/1459
See application file for complete search history.

(56) References Cited

U.S. PATENT DOCUMENTS 7,850,305 B2 * 12/2010 Hirohara ............ A61B 5/14555
351/206
2005/0078175 A1 * 4/2005 Kaneko .............. A61B 1/00009
348/65
(Continued)

FOREIGN PATENT DOCUMENTS

EP 2912991 A1 9/2015
JP 2012-69063 A 4/2010
(Continued)

OTHER PUBLICATIONS

International Preliminary Report on Patentability and Written Opinion of the International Searching Authority (forms PCT/IB/373 and PCT/ISA/237), dated Oct. 3, 2017, for corresponding International Application No. PCT/JP2016/057484, with an English translation of the Written Opinion.

(Continued)

*Primary Examiner* — Gregory M Desire
(74) *Attorney, Agent, or Firm* — Birch, Stewart, Kolasch & Birch, LLP

(57) ABSTRACT

An image signal acquisition unit acquires a first image signal corresponding to a first wavelength band, a second image signal corresponding to a second wavelength band, a third image signal corresponding to a third wavelength band, and a fourth image signal corresponding to a fourth wavelength band. A correlation storage unit stores a correlation between oxygen saturation degree and a first calculated value obtained from a specific calculation based on the second image signal, the third image signal, and the fourth image signal. A correlation correction unit calculates a correlation correction amount on the basis of the first image signal, the second image signal, the third image signal, and the fourth image signal, and corrects the correlation on the basis of the correction amount.

20 Claims, 11 Drawing Sheets

(51) Int. Cl.
*A61B 1/00* (2006.01)
*A61B 5/1455* (2006.01)
*A61B 5/1459* (2006.01)
*A61B 5/00* (2006.01)
*A61B 1/06* (2006.01)

(52) U.S. Cl.
CPC ........ *A61B 5/14551* (2013.01); *A61B 5/7235* (2013.01); *A61B 1/0638* (2013.01)

(56) References Cited

U.S. PATENT DOCUMENTS

| | | |
|---|---|---|
| 2011/0301443 A1 | 12/2011 | Yamaguchi et al. |
| 2012/0041290 A1* | 2/2012 | Perelman ............. A61B 5/0062 600/326 |
| 2012/0176486 A1 | 7/2012 | Maeda et al. |
| 2012/0289801 A1 | 11/2012 | Yamaguchi |
| 2013/0030268 A1 | 1/2013 | Saito |
| 2013/0211217 A1 | 8/2013 | Yamaguchi et al. |
| 2016/0058274 A1* | 3/2016 | Chiba .................. G01N 21/314 600/328 |
| 2018/0020903 A1* | 1/2018 | Saito ........................ A61B 1/04 382/128 |
| 2018/0049679 A1* | 2/2018 | Chiba ................ A61B 1/00009 |

FOREIGN PATENT DOCUMENTS

| | | |
|---|---|---|
| JP | 2012-143398 A | 8/2012 |
| JP | 2013-22341 A | 2/2013 |
| JP | 5426620 B2 | 2/2014 |
| JP | 2015-54062 A | 3/2015 |

OTHER PUBLICATIONS

International Search Report (form PCT/ISA/210), dated May 31, 2016, for corresponding International Application No. PCT/JP2016/057484, with an English translation.

Extended European Search Report for corresponding European Application No. 16772160.4, dated Apr. 25, 2018.

* cited by examiner

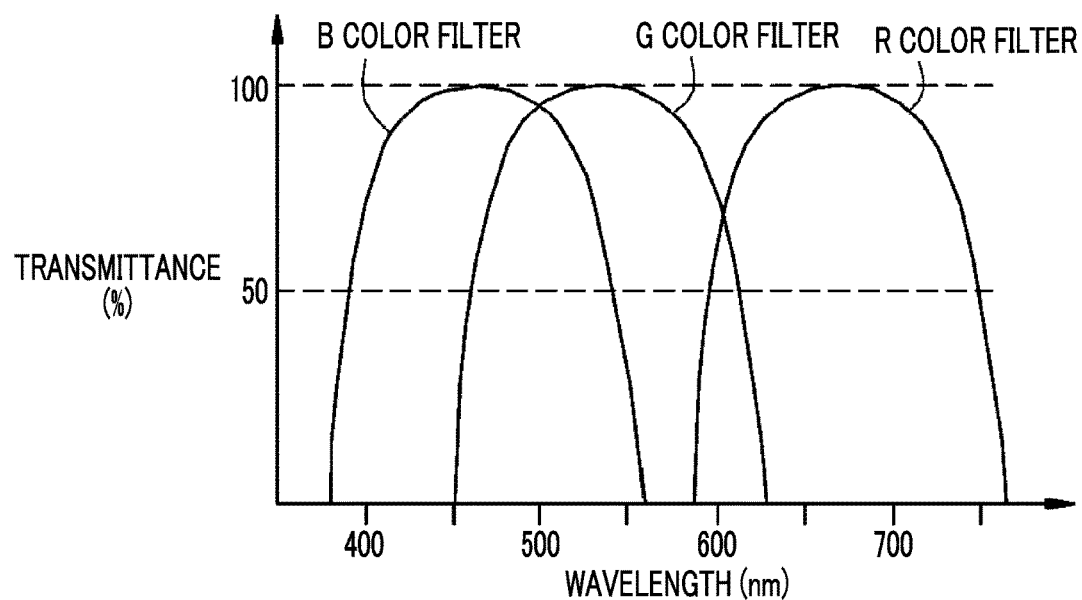

FIG. 5

| ILLUMINATION | | IMAGING (IMAGE SIGNAL) | |
|---|---|---|---|
| FIRST MEASUREMENT LIGHT EMISSION MODE | EMISSION OF SECOND BLUE LIGHT | FIRST MEASUREMENT IMAGING MODE | (B1, G1, R1) |
| SECOND MEASUREMENT LIGHT EMISSION MODE | EMISSION OF FIRST BLUE LIGHT EMISSION OF GREEN LIGHT EMISSION OF RED LIGHT | SECOND MEASUREMENT IMAGING MODE | (B2, G2, R2) |

FIG. 6

| ILLUMINATION | | IMAGING (IMAGE SIGNAL) | |
|---|---|---|---|
| FIRST CALIBRATION LIGHT EMISSION MODE | EMISSION OF FIRST BLUE LIGHT | FIRST CALIBRATION IMAGING MODE | (Bp, Gp, Rp) |
| SECOND CALIBRATION LIGHT EMISSION MODE | EMISSION OF SECOND BLUE LIGHT | SECOND CALIBRATION IMAGING MODE | (Bq, Gq, Rq) |
| THIRD CALIBRATION LIGHT EMISSION MODE | EMISSION OF GREEN LIGHT | THIRD CALIBRATION IMAGING MODE | (Br, Gr, Rr) |
| FOURTH CALIBRATION LIGHT EMISSION MODE | EMISSION OF RED LIGHT | FOURTH CALIBRATION IMAGING MODE | (Bs, Gs, Rs) |

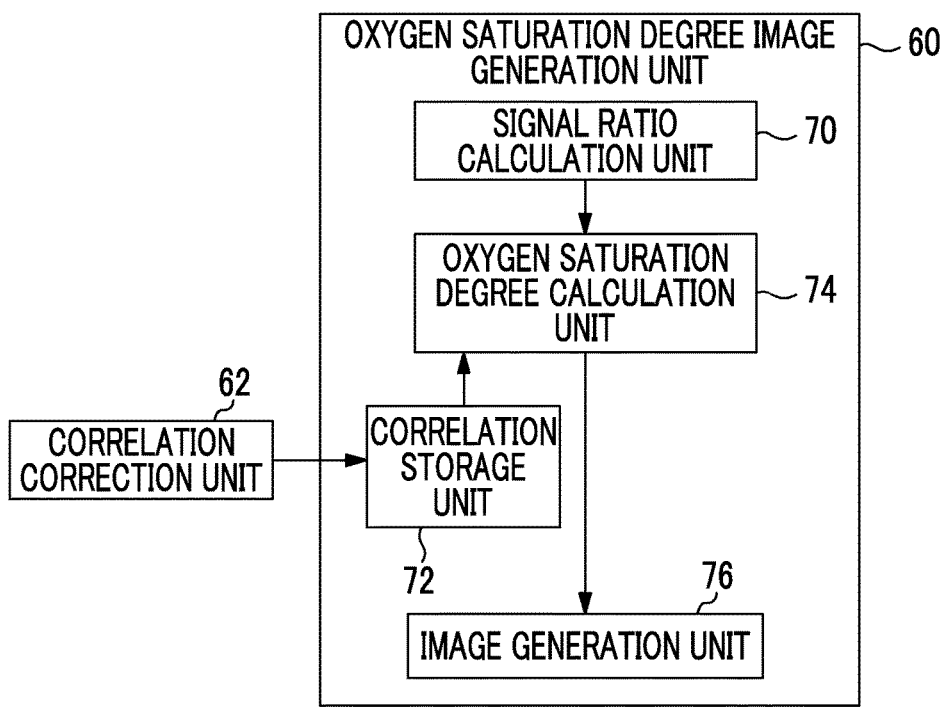
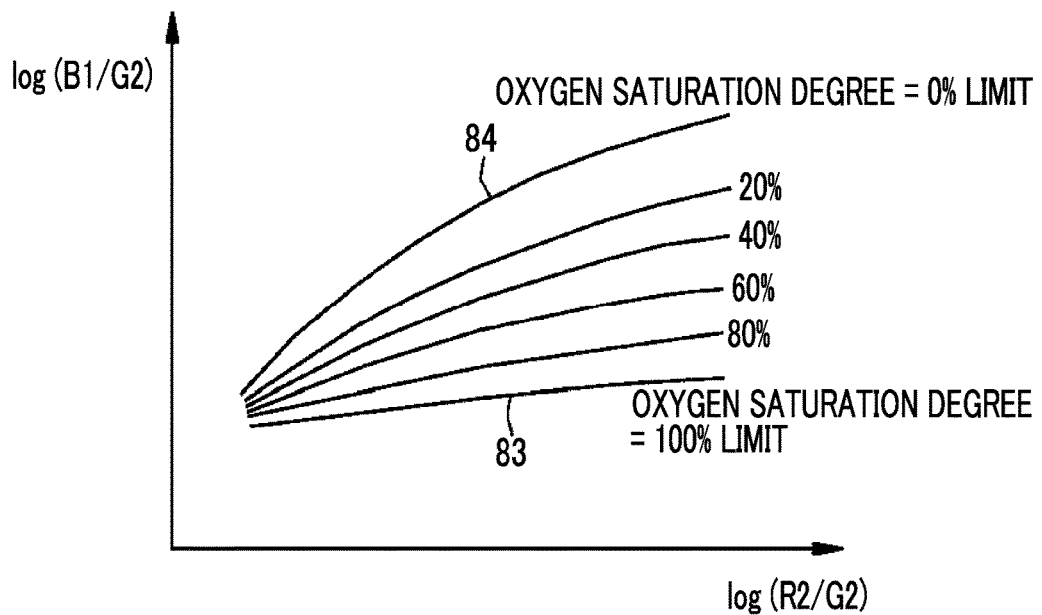

PROCESSOR DEVICE AND METHOD FOR OPERATING SAME, AND ENDOSCOPIC SYSTEM AND METHOD FOR OPERATING SAME

CROSS-REFERENCE TO RELATED APPLICATIONS

This application is a Continuation-in-part of PCT International Application No. PCT/JP 2016/057484 filed on Mar. 10, 2016, which claims priority under 35 U.S.C § 119(a) to Japanese Patent Application No. 2015-075888 filed on Apr. 2, 2015 and Japanese Patent Application No. 2016-005911 filed on Jan. 15, 2016. Each of the above application(s) is hereby expressly incorporated by reference, in its entirety, into the present application.

BACKGROUND OF THE INVENTION

1. Field of the Invention

The present invention relates to a processor device and a method for operating the same and an endoscopic system and a method for operating the same that calculate the oxygen saturation degree of an observation target.

2. Description of the Related Art

In the medical field, it is general to perform diagnosis using endoscopic systems including a light source device, an endoscope, and a processor device. Particularly, endoscopic systems for obtaining an observation image in which specific tissues or structures, such as blood vessels or duct structures, are emphasized not only by simply imaging an observation target but also by devising the wavelength of illumination light to be radiated to the observation target or by performing signal processing, such as spectrum estimation processing, on image signals obtained by imaging the observation target have become widespread.

Additionally, in recent years, there are also endoscopic systems for obtaining living body functional information on the basis of the image signals obtained by imaging the observation target. For example, diagnosis of a lesioned site using the oxygen saturation degree of hemoglobin in blood has been performed. As a method for acquiring the oxygen saturation degree, for example, as illustrated in JP2013-22341A (JP5426620B), there is a method for calculating the oxygen saturation degree using a correlation between a plurality of image signals including at least image signals obtained by radiating light in a wavelength band where the light absorption coefficients of an oxygenated hemoglobin and a reduced hemoglobin are different from each other to an observation target, and the oxygen saturation degree.

The correlation between the plurality of image signals and the oxygen saturation degree as described above may vary due to various factors, such as various sites such as the esophagus, the stomach, and the large intestine, and differences among patients such as men and women, and adults and children. In contrast, in JP2013-22341A (JP5426620B), the oxygen saturation degree is pre-measured by performing pre-imaging of imaging particularly a normal part of the observation target before observation of the inside of the body by the oxygen saturation degree is actually performed. Then, a difference between the pre-measured oxygen saturation degree and a reference value (for example, 70%) of the oxygen saturation degree in the normal part is calculated, and the correlation is corrected on the basis of this calculated difference. By correcting such a correlation, it is possible to accurately calculate the oxygen saturation degree without being influenced by sites or patients.

SUMMARY OF THE INVENTION

In JP2013-22341A (JP5426620B), the reference value of the oxygen saturation degree in the normal part is set to a constant value, such as 70%. However, the reference value of the oxygen saturation degree in this normal part may vary depending on various sites or differences between patients. Additionally, in JP2013-22341A (JP5426620B), the correlation is corrected after mucus including a yellow (or yellowish-brown) pigment, such as bilirubin or stercobilin, is cleaned. However, there may be a case where it is not possible to completely clean the mucus, such as the yellow pigment. In this case, even if the correlation is corrected, it is difficult to accurately calculate the oxygen saturation degree.

An object of the invention is to provide a processor device and a method for operating the same, and an endoscopic system and a method for operating the same, capable of accurately calculating oxygen saturation degree in a situation where a yellow pigment or the like is present in an observation target in addition to a case where there are various sites or patients are different.

A processor device of the invention comprises an image signal acquisition unit that acquires a first image signal corresponding to a first wavelength band whose light absorption amount varies according to a density of a pigment other than hemoglobin among pigments included in an observation target, a second image signal corresponding to a second wavelength band whose light absorption amount varies according to an oxygen saturation degree of the hemoglobin included in the observation target, a third image signal corresponding to a third wavelength band that has a wavelength longer than the first wavelength band and the second wavelength band and whose light absorption amount varies according to an amount of blood, and a fourth image signal corresponding to a fourth wavelength band that has a wavelength longer than the third wavelength band; a correlation storage unit that stores a correlation between a first calculated value obtained by a specific calculation based on the second image signal, the third image signal, and the fourth image signal, and the oxygen saturation degree; and a correlation correction unit that calculates a correction amount of the correlation on the basis of the first image signal, the second image signal, the third image signal, and the fourth image signal, and corrects the correlation on the basis of the correction amount.

It is preferable that the correlation correction unit includes a living body internal information calculation unit that calculates information in a living body of the observation target on the basis of a first signal ratio between the first image signal and the third image signal, a second signal ratio between the second image signal and the third image signal, and a third signal ratio between the fourth image signal and the third image signal, a correction amount calculation unit that calculates the correction amount on the basis of predetermined reference information and the living body internal information, and a correction unit that corrects the correlation on the basis of the correction amount.

It is preferable that, in a feature space for correction having a second calculated value obtained by calculation for correction based on the first signal ratio and the second signal ratio as a first axis and having the third signal ratio as a second axis, the reference information is distributed on a reference line, and the living body internal information is distributed on an actual measurement line at a position different from the reference line, and the correction amount is calculated on the basis of a difference between the reference line and the actual measurement line.

It is preferable that the reference information is information obtained in a case where there is no influence of the pigment other than hemoglobin, and is information that does not vary depending on the oxygen saturation degree, and the living body internal information is information that varies according to the density of the pigment other than hemoglobin, and is information that is constant with respect to the oxygen saturation degree.

It is preferable that the first wavelength band has an isosbestic wavelength where light absorption coefficients of an oxygenated hemoglobin and a reduced hemoglobin are the same. It is preferable that the pigment other than hemoglobin is yellow pigment. It is preferable that the first wavelength band is 450±10 nm, the second wavelength band is 470±10 nm, the third wavelength band is 540±20 nm, and the fourth wavelength band is 640±20 nm.

It is preferable that the image signal acquisition unit acquires the first image signal, the second image signal, the third image signal, and the fourth image signal in a calibration mode where the correlation is corrected, and acquires the second image signal, the third image signal, and the fourth image signal in an oxygen saturation degree mode where the oxygen saturation degree is calculated, calculation of the correction amount and correction of the correlation are performed in the correlation correction unit on the basis of the first image signal, the second image signal, the third image signal, and the fourth image signal that are acquired in the calibration mode, and the oxygen saturation degree is calculated in an oxygen saturation degree calculation unit with reference to a corrected correlation on the basis of the second image signal, the third image signal, and the fourth image signal that are acquired in the oxygen saturation degree mode.

An endoscopic system of the invention compresses the processor device of the invention described above, and a light source device having a first semiconductor light source that emits light in the first wavelength band, a second semiconductor light source that emits light in the second wavelength band, a third semiconductor light source that emits light in the third wavelength band, and a fourth semiconductor light source that emits light in the fourth wavelength band.

An endoscopic system comprises the processor device of the invention described above; and a broadband light source that emits white light, and a light source device having a rotation filter provided with a first filter that allows light in the first wavelength band of the white light to be transmitted therethrough, a second filter that allows light in the second wavelength band of the white light to be transmitted therethrough, a third filter that allows light of the third wavelength band of the white light to be transmitted therethrough, and a fourth filter that allows light of the fourth wavelength band of the white light to be transmitted therethrough.

A method for operating a processor device of the invention comprises a first image signal acquisition step of causing an image signal acquisition unit to acquire a first image signal corresponding to a first wavelength band whose light absorption amount varies according to a density of a pigment other than hemoglobin among pigments included in an observation target, a second image signal corresponding to a second wavelength band whose light absorption amount varies according to an oxygen saturation degree of the hemoglobin included in the observation target, a third image signal corresponding to the third wavelength band that has a wavelength longer than the first wavelength band and the second wavelength band and whose light absorption amount varies according to an amount of blood, and a fourth image signal corresponding to a fourth wavelength band that has a wavelength longer than the third wavelength band; and a correlation correction step of causing a correlation correction unit to calculate a correction amount of a correlation between a first calculated value obtained by a specific calculation based on the second image signal, the third image signal, and the fourth image signal, and the oxygen saturation degree on the basis of the first image signal, the second image signal, the third image signal, and the fourth image signal, and to correct the correlation on the basis of the correction amount. It is preferable that the correlation correction step includes a living body internal information calculation step of causing a living body internal information calculation unit to calculate information in a living body of the observation target on the basis of a first signal ratio between the first image signal and the third image signal, a second signal ratio between the second image signal and the third image signal, and a third signal ratio between the fourth image signal and the third image signal, a correction amount calculation step of causing a correction amount calculation unit to calculate the correction amount on the basis of predetermined reference information and the living body internal information, and a correction step of causing a correction unit to correct the correlation on the basis of the correction amount.

It is preferable that, in the method for operating a processor device of the invention described above in which, in the first image signal acquisition step, the image signal acquisition unit acquires the first image signal, the second image signal, the third image signal, and the fourth image signal in a calibration mode where the correlation is corrected, and in the correlation correction step, the correlation correction unit performs calculation of the correction amount and correction of the correlation on the basis of the first image signal, the second image signal, the third image signal, and the fourth image signal that are acquired in the calibration mode, the method further comprises a second image signal acquisition step of causing the image signal acquisition unit to acquire the second image signal, the third image signal, and the fourth image signal in an oxygen saturation degree mode where the oxygen saturation degree is calculated; and an oxygen saturation degree calculation step of causing an oxygen saturation degree calculation unit to calculate the oxygen saturation degree with reference to a corrected correlation on the basis of the second image signal, the third image signal, and the fourth image signal that are acquired in the oxygen saturation degree mode.

A method for operating an endoscopic system of the invention comprises a light emission step of causing a light source device to sequentially emit light in a first wavelength band whose light absorption amount varies according to a density of a pigment other than hemoglobin among pigments included in an observation target, light in a second wavelength band whose light absorption amount varies according to an oxygen saturation degree of the hemoglobin included in the observation target, light in a third wavelength band that has a wavelength longer than the first wavelength band and the second wavelength band and whose light absorption amount varies according to an amount of blood, and light in a fourth wavelength band that has a wavelength longer than the third wavelength band, a first image signal acquisition step of causing an image signal acquisition unit to acquire a first image signal corresponding to the first wavelength band, a second image signal corresponding to the second wavelength band, a third image signal corresponding to the third wavelength band, and a fourth image signal corresponding to the fourth wavelength band; and a correlation correction step of causing a correlation correction unit to calculate a correction amount of a correlation between a first calculated value obtained by a specific calculation based on the second image signal, the third image signal, and the fourth image signal, and the oxygen saturation degree on the basis of the first image signal, the second image signal, the third image signal, and the fourth image signal, and to correct the correlation on the basis of the correction amount. It is preferable that the correlation correction step includes a living body internal information calculation step of causing a living body internal information calculation unit to calculate information in a living body of the observation target on the basis of a first signal ratio between the first image signal and the third image signal, a second signal ratio between the second image signal and the third image signal, and a third signal ratio between the fourth image signal and the third image signal, a correction amount calculation step of causing a correction amount calculation unit to calculate the correction amount on the basis of predetermined reference information and the living body internal information, and a correction step of causing a correction unit to correct the correlation on the basis of the correction amount.

It is preferable that, in the method for operating an endoscopic system of the invention described above in which, in the first image signal acquisition step, the image signal acquisition unit acquires the first image signal, the second image signal, the third image signal, and the fourth image signal in a calibration mode where the correlation is corrected, and in the correlation correction step, the correlation correction unit performs calculation of the correction amount and correction of the correlation on the basis of the first image signal, the second image signal, the third image signal, and the fourth image signal that are acquired in the calibration mode, the method further comprises a second image signal acquisition step of causing the image signal acquisition unit to acquire the second image signal, the third image signal, and the fourth image signal in an oxygen saturation degree mode where the oxygen saturation degree is calculated; and an oxygen saturation degree calculation step of causing an oxygen saturation degree calculation unit to calculate the oxygen saturation degree with reference to a corrected correlation on the basis of the second image signal, the third image signal, and the fourth image signal that are acquired in the oxygen saturation degree mode.

According to the invention, the oxygen saturation degree can be accurately calculated even in a situation where the yellow pigment or the like is present on the observation target in addition to a case where there are various sites or patients are different.

BRIEF DESCRIPTION OF THE DRAWINGS

FIG. 3 is a graph illustrating the spectral sensitivity of an imaging sensor.
FIG. 4 is an explanatory view illustrating emission of illumination light and imaging of an observation target in a normal mode.
FIG. 5 is an explanatory view illustrating emission of the illumination light and imaging of the observation target in an oxygen saturation degree mode.
FIG. 6 is an explanatory view illustrating emission of the illumination light and imaging of the observation target in a calibration mode.
FIG. 7 is a block diagram illustrating the functions of an oxygen saturation degree image generation unit.
FIG. 8 is a graph illustrating the positions of isograms of oxygen saturation degree in a first feature space in which a vertical axis represents Log(B1/G2) and a horizontal axis represents Log(R2/G2).

DESCRIPTION OF THE PREFERRED EMBODIMENTS

First Embodiment

Figure 1:
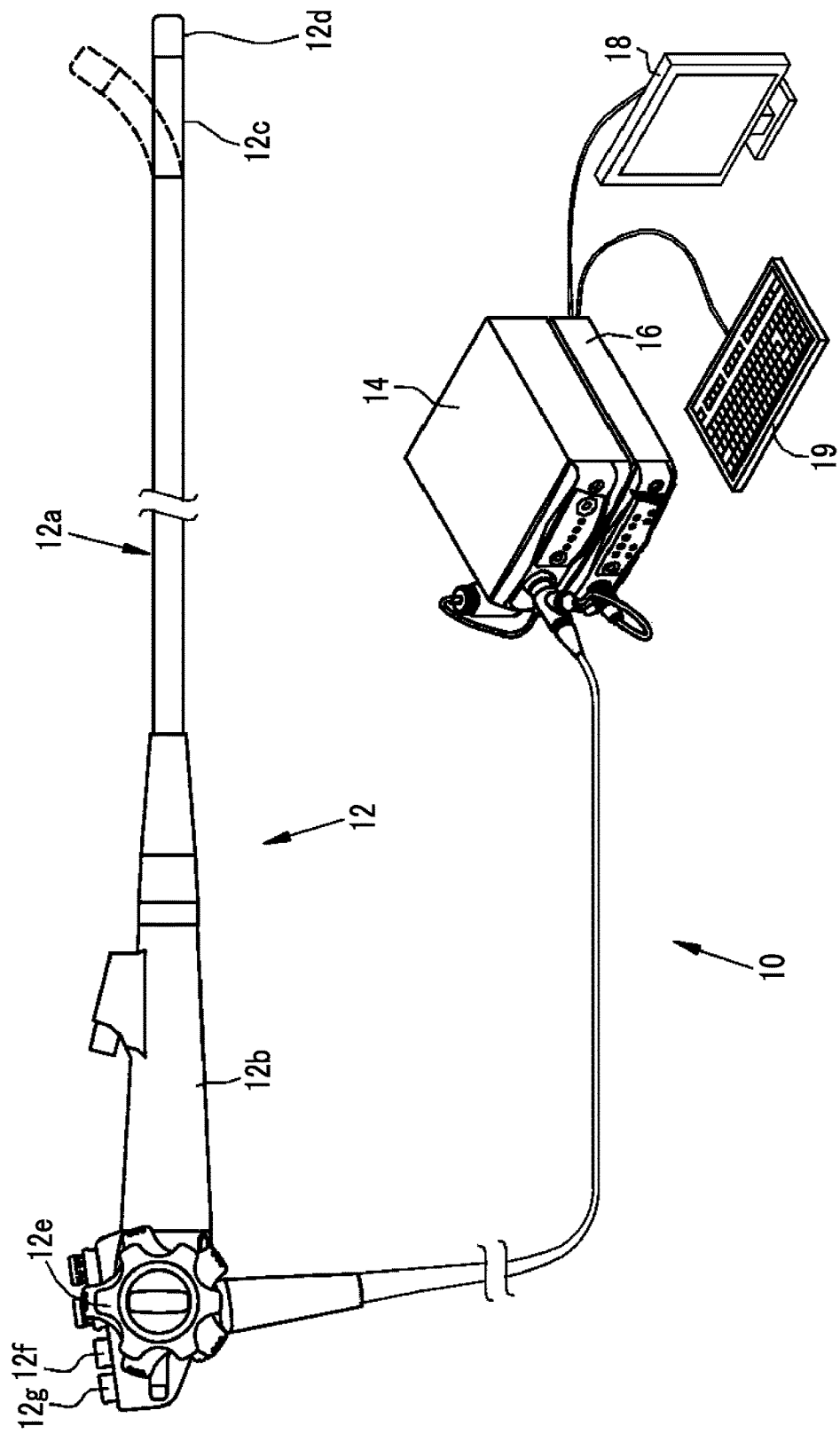
FIG. 1 is an external view of an endoscopic system.

In FIG. 1, an endoscopic system 10 has an endoscope 12, a light source device 14, a processor device 16, a monitor 18, and a console 19. The endoscope 12 is optically connected to the light source device 14 and is electrically connected to the processor device 16. The endoscope 12 has an insertion part 12a to be inserted into the body of an observation target, an operating part 12b provided at a base end portion of the insertion part 12a, and a bending part 12c and a distal end part 12d provided on a distal end side of the insertion part 12a. By operating an angle knob 12e of the operating part 12b, the bending part 12c makes a bending motion. The distal end part 12d is directed in a desired direction by this bending motion of the bending part 12c. In addition, the distal end part 12d is provided with a jet port (not illustrated) that jets a cleaning liquid toward the observation target.

Additionally, the operating part 12b is provided with a mode switchover switch (mode switchover SW) 12f used for a switching operation in an observation mode and a still image acquisition instruction unit 12g used for an instruction for acquiring a still image of the observation target, in addition to the angle knob 12e.

The endoscopic system 10 has three observation modes of a normal mode, an oxygen saturation degree mode, and a calibration mode. In the normal mode, a natural-tone image (hereinafter, referred to as a normal image) obtained by imaging the observation target using white light for illumination light is displayed on the monitor 18. In the oxygen saturation degree mode, the oxygen saturation degree of the observation target is measured using a correlation between image signals obtained by imaging the observation target and the oxygen saturation degree, and an image (hereinafter referred to as an oxygen saturation degree image) obtained by imaging the measured oxygen saturation degree in a pseudo-color or the like is displayed on the monitor 18. In the calibration mode, pre-imaging for imaging the observation target before the oxygen saturation degree is measured by the oxygen saturation degree mode is performed, and a correction amount ΔD of the correlation to be used during the measurement of the oxygen saturation degree is calculated from image signals obtained by this pre-imaging. Additionally, in the calibration mode, the correlation is corrected on the basis of the correction amount ΔD.

The processor device 16 is electrically connected to the monitor 18 and the console 19. The monitor 18 outputs and displays the image of the observation target, information accompanying the image of the observation target, and the like. The console 19 functions as a user interface that receives an input operation, such as function setting. In addition, an external recording unit (not illustrated) that records an image, image information, and the like may be connected to the processor device 16.

Figure 2:
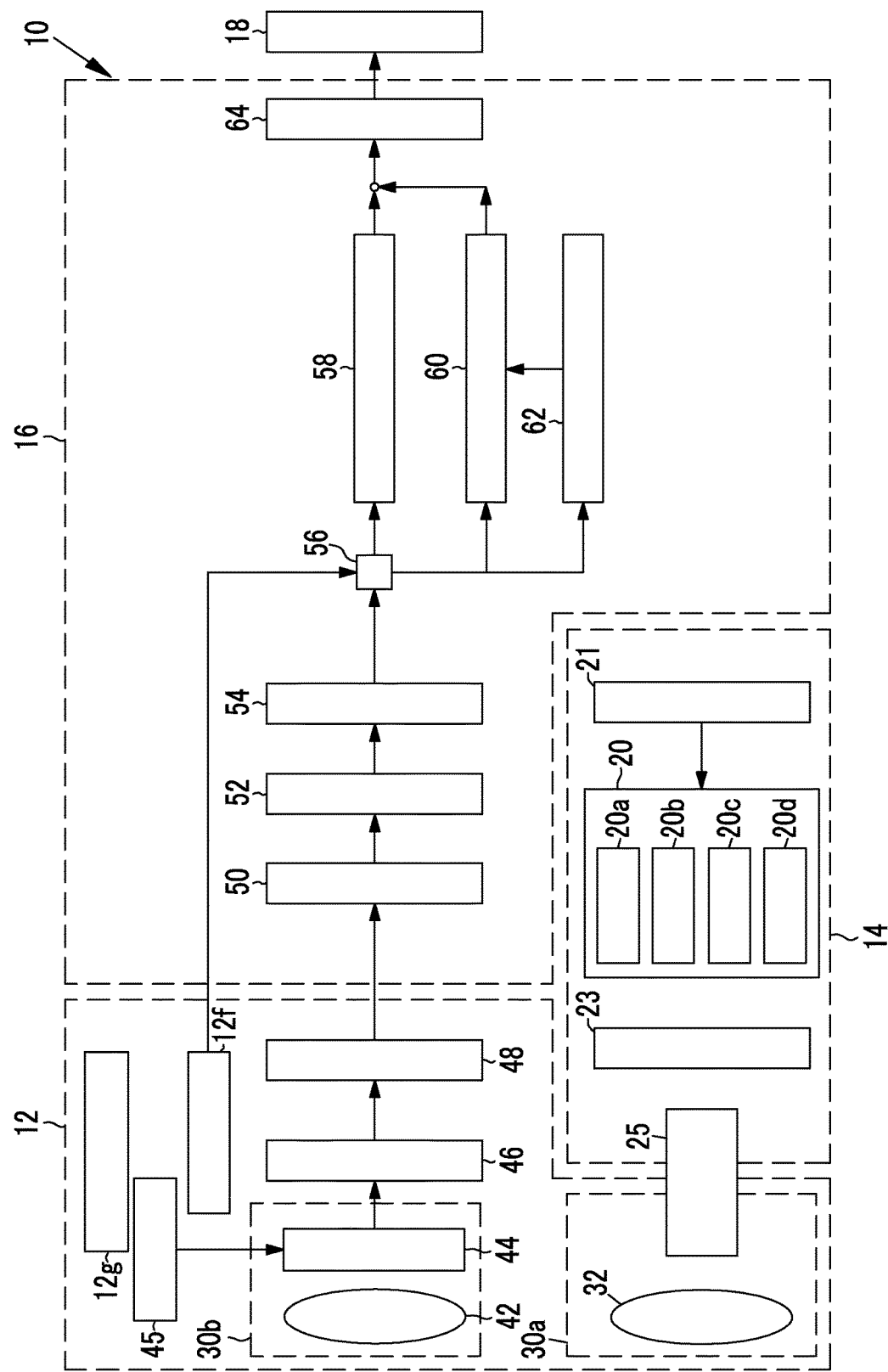
FIG. 2 is a block diagram illustrating the functions of the endoscopic system of the first embodiment.

In FIG. 2, the light source device 14 includes a light source 20, and a light source control unit 21 that controls the light source 20. The light source 20 has, for example, a plurality of semiconductor light sources, switches on or off these semiconductor light sources, respectively, and emits illumination light for illuminating the observation target by controlling the light emission amounts of the respective semiconductor light sources in a case where the semiconductor light sources are switched on. In the present embodiment, the light source 20 has four color LEDs of a blue short-wavelength light emitting diode (BS-LED) 20a, a blue long-wavelength light emitting diode (BL-LED) 20b, a green light emitting diode (G-LED) 20c, and a red light emitting diode (R-LED) 20d.

The BS-LED 20a (corresponding to a "first semiconductor light source" of the invention) emits first blue light BS with a wavelength band of 450±10 nm. The BL-LED 20b (corresponding to a "second semiconductor light source" of the invention) emits second blue light BL with a wavelength band of 470±10 nm. The G-LED 20c (corresponding to a "third semiconductor light source" of the invention) emits green light G with a wavelength band of 540±10 nm. The R-LED 20d (corresponding to a "fourth semiconductor light source" of the invention) emits red light R with a wavelength band of 640±20 nm. In addition, center wavelengths and peak wavelengths in the LEDs 20a to 20d may be the same as each other or may be different from each other.

The light source control unit 21 independently controls turning-on or turning-off of the LEDs 20a to 20d, light emission amounts during switching on, and the like by independently inputting control signals to the LEDs 20a to 20d. Turning-on or turning-off control in the light source control unit 21 varies in the respective modes. In the normal mode, the first blue light BS, the green light and the red light R are simultaneously emitted by simultaneously turning on the BS-LED 20a, the G-LED 20c, and the R-LED 20d. In the oxygen saturation degree mode, a first measurement light emission mode where the second blue light BL is emitted by turning on the BL-LED 20b, and a second measurement light emission mode where the first blue light BS, the green light and the red light R are simultaneously emitted by simultaneously turning on the BS-LED 20a, the G-LED 20c, and the R-LED 20d are alternately repeated.

In the calibration mode, the first blue light BS, the second blue light BL, the green light and the red light R are sequentially emitted by sequentially turning on the BS-LED 20a, the BL-LED 20b, the G-LED 20c, and the R-LED 20d.

In this calibration mode, a mode where the first blue light BS is emitted is defined as a first calibration light emission mode, a mode where the second blue light BL is emitted is defined as a second calibration light emission mode, a mode where the green light G is emitted is defined as a third calibration light emission mode, and a mode where the red light R is emitted is defined as a fourth calibration light emission mode.

The lights emitted from the respective LEDs 20a to 20d enter a light guide 25 via an optical path coupling unit 23 composed of a mirror, a lens, and the like. The light guide 25 is built in the endoscope 12 and a universal cord (a cord that connects the endoscope 12, and the light source device 14 and the processor device 16 together). The light guide 25 propagates the light from the light guide 25, to the distal end part 12d of the endoscope 12.

The distal end part 12d of the endoscope 12 is provided with an illumination optical system 30a and an imaging optical system 30b. The illumination optical system 30a has an illumination lens 32, and the illumination light propagated by the light guide 25 is radiated to the observation target via the illumination lens 32. The imaging optical system 30b has an objective lens 42 and an imaging sensor 44. The light from the observation target to which the illumination light has been radiated enters the imaging sensor 44 via the objective lens 42. Accordingly, the image of the observation target is formed on the imaging sensor 44.

The imaging sensor 44 is a color imaging sensor that images the observation target under illumination with the illumination light. Pixels of the imaging sensor 44 are respectively provided with a blue pixel (B pixel) having a blue (B) color filter, a green pixel (G pixel) having a green (G) color filter, or a red pixel (R pixel) having a red (R) color filter. As illustrated in FIG. 3, the B color filter allows mainly blue band light, specifically, light in a wavelength band of 380 to 560 nm to be transmitted therethrough. A peak wavelength at which the transmittance becomes maximum is present in the vicinity of 460 to 470 nm. The G color filter allows mainly green band light, specifically, light in a wavelength band of 450 to 630 nm to be transmitted therethrough. The R color filter allows mainly red band light, specifically, light 580 to 760 nm to be transmitted therethrough.

As the imaging sensor 44, a charge coupled device (CCD) imaging sensor or a complementary metal-oxide semiconductor (CMOS) imaging sensor is available. Additionally, instead of the primary color imaging sensor 44, a complementary color imaging sensor including complementary color filters in C (cyan), M (magenta), Y (yellow), and G (green) may be used. In a case where the complementary color imaging sensor is used, image signals in four colors of CMYG are output. Thus, image signals in respective colors of RGB that are the same colors as those of the imaging sensor 44 can be obtained by converting the image signals in four colors of CMYG into the image signals in three colors of RGB through color conversion of complementary color to primary color.

Driving of the imaging sensor 44 is controlled by an imaging control unit 45. The control in the imaging control unit 45 varies in the respective modes. As illustrated in FIG. 4, in the normal mode, the imaging control unit 45 controls the imaging sensor 44 so as to image the observation target under illumination for each frame with the first blue light BS, the green light and the red light R. As a result, a Bc image signal is output from the B pixel of the imaging sensor 44, a Gc image signal is output from the G pixel of the imaging sensor 44, and an Rc image signal is output from the R pixel of the imaging sensor 44.

As illustrated in FIG. 5, in the oxygen saturation degree mode, a first measurement imaging mode where the observation target under illumination is imaged by one frame with the second blue light BL in the first measurement light emission mode, and a second measurement imaging mode where the observation target under illumination is imaged by one frame with the first blue light BS, the green light G, and the red light R in the second measurement light emission mode are alternately repeated by the control of the imaging control unit 45 on the imaging sensor 44. Accordingly, in the first measurement imaging mode, a B1 image signal is output from the B pixel of the imaging sensor 44, a G1 image signal is output from the G pixel of the imaging sensor 44, and an R1 image signal is output from the R pixel of the imaging sensor 44. In the second measurement imaging mode, a B2 image signal is output from the B pixel of the imaging sensor 44, a G2 image signal is output from the G pixel of the imaging sensor 44, and an R2 image signal is output from the R pixel of the imaging sensor 44.

As illustrated in FIG. 6, in the calibration mode, a first calibration imaging mode where the observation target under illumination is imaged by one frame with first blue light BS in the first calibration light emission mode, a second calibration imaging mode where the observation target under illumination is imaged by one frame with the second blue light BL in the second calibration light emission mode, a third calibration imaging mode where the observation target under illumination is imaged by one frame with the green light G in the third calibration light emission mode, and a fourth calibration imaging mode where the observation target under illumination is imaged by one frame with the red light R in the fourth calibration light emission mode are sequentially performed by the control of the imaging control unit 45 on the imaging sensor 44.

Accordingly, in the first calibration imaging mode, a Bp image signal is output from the B pixel of the imaging sensor 44, a Gp image signal is output from the G pixel of the imaging sensor 44, and an Rp image signal is output from the R pixel of the imaging sensor 44. Additionally, in the second calibration imaging mode, a Bq image signal is output from the B pixel of the imaging sensor 44, a Gq image signal is output from the G pixel of the imaging sensor 44, and an Rq image signal is output from the R pixel of the imaging sensor 44. Additionally, in the third calibration imaging mode, a Br image signal is output from the B pixel of the imaging sensor 44, a Gr image signal is output from the G pixel of the imaging sensor 44, and an Rr image signal is output from the R pixel of the imaging sensor 44. Additionally, in the fourth calibration imaging mode, a Bs image signal is output from the B pixel of the imaging sensor 44, a Gs image signal is output from the G pixel of the imaging sensor 44, and an Rs image signal is output from the R pixel of the imaging sensor 44.

As illustrated in FIG. 2, a correlated double sampling/automatic gain control (CDS/AGC) circuit 46 performs correlation double sampling (CDS) and automatic gain control (AGC) on analog image signals obtained from the imaging sensor 44. The image signals that have passed through the CDS/AGC circuit 46 are converted into digital image signals by an analog/digital (A/D) converter 48. The digital image signals after the A/D conversion are input to the processor device 16.

The processor device 16 includes an image signal acquisition unit 50, a digital signal processor (DSP) 52, a noise reduction unit 54, an image processing switching unit 56, a normal image generation unit 58, an oxygen saturation degree image generation unit 60, a correlation correction unit 62, and a video signal generation unit 64. The image signal acquisition unit 50 receives the image signals input from the endoscope 12 and transmits the received image signals to the DSP 52.

The DSP 52 performs various kinds of signal processing, such as defect correction processing, offset processing, gain correction processing, linear matrix processing, gamma conversion processing, demosaic processing, and YC conversion processing, on the received image signals. In the defect correction processing, a signal of a defective pixel of the imaging sensor 44 is corrected. In the offset processing, a dark current component is removed from an image signal subjected to the defect correction processing, and an accurate zero level is set. In the gain correction processing, a signal level of each image signal is adjusted by multiplying an image signal of each color after the offset processing by a specific gain. The linear matrix processing for enhancing color reproducibility is performed on the image signal of each color after the gain correction processing.

Then, the brightness and the saturation of each image signal are adjusted by the gamma conversion processing.

The demosaic processing (also referred to as isotropic processing or synchronization processing) is performed on the image signal after the linear matrix processing, and a signal of a missing color of each pixel is created by interpolation. By means of the demosaic processing, all pixels have signals of respective RGB colors. The DSP 52 performs the YC conversion processing on each image signal after the demosaic processing, and outputs a luminance signal Y, a color difference signal Cb, and a color difference signal Cr to the noise reduction unit 54.

The noise reduction unit 54 performs noise reduction processing using, for example, a moving average method, a median filter method, or the like on the image signal subjected to the demosaic processing or the like by the DSP 52. The image signal from which noise is reduced is input in the image processing switching unit 56.

The image processing switching unit 56 switches a transmission destination of the image signal from the noise reduction unit 54 to any of the normal image generation unit 58, the oxygen saturation degree image generation unit 60, or the correlation correction unit 62, depending on a set mode. Specifically, in a case where the normal mode is set, the image signal from the noise reduction unit 54 is input to the normal image generation unit 58. Additionally, in a case where the oxygen saturation degree mode is set, the image signal from the noise reduction unit 54 is input to the oxygen saturation degree image generation unit 60. Additionally, in a case where the calibration mode is set, the image signal from the noise reduction unit 54 is input to the correlation correction unit 62.

The normal image generation unit 58 further performs color conversion processing, such as 3×3 matrix processing, grayscale conversion processing, or three-dimensional look-up table (LUT) processing, on the Rc image signal, the Gc image signal, and the Bc image signal equivalent to one input frame. Then, various kinds of color emphasis processing are performed on RGB image data subjected to the color conversion processing. Structure emphasis processing, such as spatial frequency emphasis, is performed on the RGB image data subjected to the color emphasis processing. The RGB image data subjected to the structure emphasis processing is input to the video signal generation unit 64 as a normal image.

The oxygen saturation degree image generation unit 60 calculates the oxygen saturation degree, using a correlation between the B1 image signal (corresponding to a "second image signal" of the invention), the G2 image signal (corresponding to a "third image signal" of the invention), the R2 image signal (corresponding to a "fourth image signal" of the invention) among image signals obtained in the oxygen saturation degree mode, and the oxygen saturation degree. A method for calculating the oxygen saturation degree will be described below. The oxygen saturation degree image in which the calculated oxygen saturation degree is imaged with a pseudo-color or the like is generated. This oxygen saturation degree image is input to the video signal generation unit 64.

The correlation correction unit 62 corrects the correlation used for calculating the oxygen saturation degree, in order to eliminate the influence of a yellow pigment in addition to a difference of a site of the observation target and a difference between patients. Specifically, the correlation correction unit 62 calculates the correction amount ΔD of the correlation on the basis of the Bp image signal (corresponding to a "first image signal" of the invention), the Bq image signal (corresponding to the "second image signal" of the invention), the Gr image signal (corresponding to the "third image signal" of the invention), and the Rs image signal (corresponding to the "fourth image signal" of the invention), among the image signals obtained in the calibration mode, and corrects the correlation on the basis of the calculated correction amount ΔD. A method for correcting the correlation will be described below.

The video signal generation unit 64 converts image data on the normal image from the normal image generation unit 58 or image data on the oxygen saturation degree image from the oxygen saturation degree image generation unit 60 into video signals that enables full color display on the monitor 18. The converted video signals are input to the monitor 18. Accordingly, the normal image or the oxygen saturation degree image is displayed on the monitor 18.

As illustrated in FIG. 7, the oxygen saturation degree image generation unit 60 includes a signal ratio calculation unit 70, a correlation storage unit 72, an oxygen saturation degree calculation unit 74, and an image generation unit 76. The signal ratio calculation unit 70 calculates a signal ratio used for calculating the oxygen saturation degree in the oxygen saturation degree calculation unit 74. Specifically, the signal ratio calculation unit 70 calculates a signal ratio B1/G2 of the B1 image signal and the G2 image signal, a signal ratio R2/G2 of the R2 image signal and the G2 image signal, and a signal ratio G2/B2 of the G2 image signal and the B2 image signal, respectively, for each pixel.

The correlation storage unit 72 stores a correlation between the signal ratios calculated by the signal ratio calculation unit 70, and the oxygen saturation degree in a storage unit, such as a look-up table (LUT). In a case where the correlation is expressed on a first feature space formed by a vertical axis Log(B1/G2) and a horizontal axis Log (R2/G2), as illustrated in FIG. 8, isograms obtained by connecting portions with the same oxygen saturation degree together are formed substantially in a horizontal axis direction on the first feature space. Additionally, the isograms are located closer to a lower side in a vertical axis direction as the oxygen saturation degree becomes larger. For example, a isogram 83 whose oxygen saturation degree is 100% is located below a isogram 84 whose oxygen saturation degree is 0%.

In addition, the positions and the shapes of the isograms in the first feature space are obtained in advance by physical simulation of light scattering. Additionally, the correlations between the signal ratio B1/G2 and R2/G2 and the oxygen saturation degree is stored in the correlation storage unit 72. However, the invention is not limited to the correlations with the signal ratio B1/G2 and R2/G2, and a correlation between a first calculated value obtained by performing specific calculation (for example, difference processing) based on the B1 image signal, the G2 image signal, and the R2 image signal, and the oxygen saturation degree may be stored.

Figure 9:
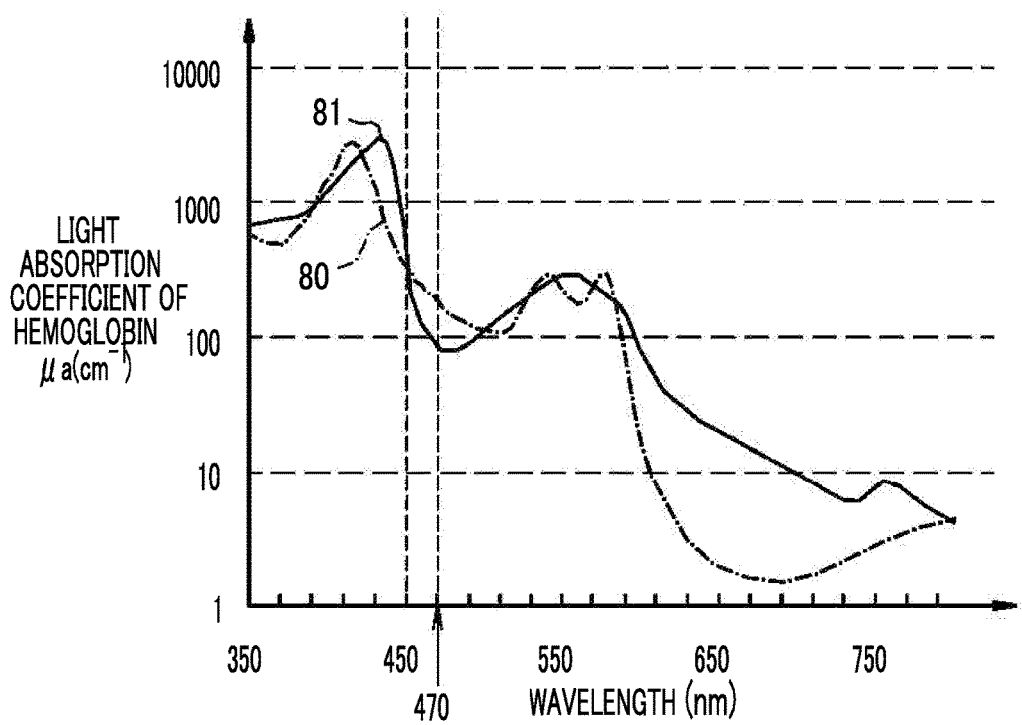
FIG. 9 is a graph illustrating the light absorption coefficients of an oxygenated hemoglobin and a reduced hemoglobin.

The above correlation is closely correlated with light-absorption characteristics and light-scattering characteristics of an oxygenated hemoglobin (graph 80) and a reduced hemoglobin (graph 81) that are illustrated in FIG. 9. For example, in a wavelength band with a large difference between the light absorption coefficients of the oxygenated hemoglobin and the reduced hemoglobin like the wavelength band 470±10 nm of the second blue light BL, light absorption amount varies depending on the oxygen saturation degree of hemoglobin. Therefore, it is easy to handle information on the oxygen saturation degree. Hence, it is possible to calculate the oxygen saturation degree by using the signal ratio B1/G2 including the B1 image signal corresponding to the second blue light BL with a center wavelength of 470 nm. However, the signal ratio B1/G2 has a high dependence on not only the oxygen saturation degree but the amount of blood. Thus, by using the signal ratio R2/G2 that vary mainly depending on the amount of blood in addition to the signal ratio B1/G2, it is possible to accurately obtain the oxygen saturation degree without being influenced by the amount of blood. In addition, since the wavelength band of 540±20 nm of the green light included in the G2 image signal has a relatively high light absorption coefficient of hemoglobin, the wavelength band is a wavelength band where the light absorption amount easily varies depending on the amount of blood.

Figure 10:
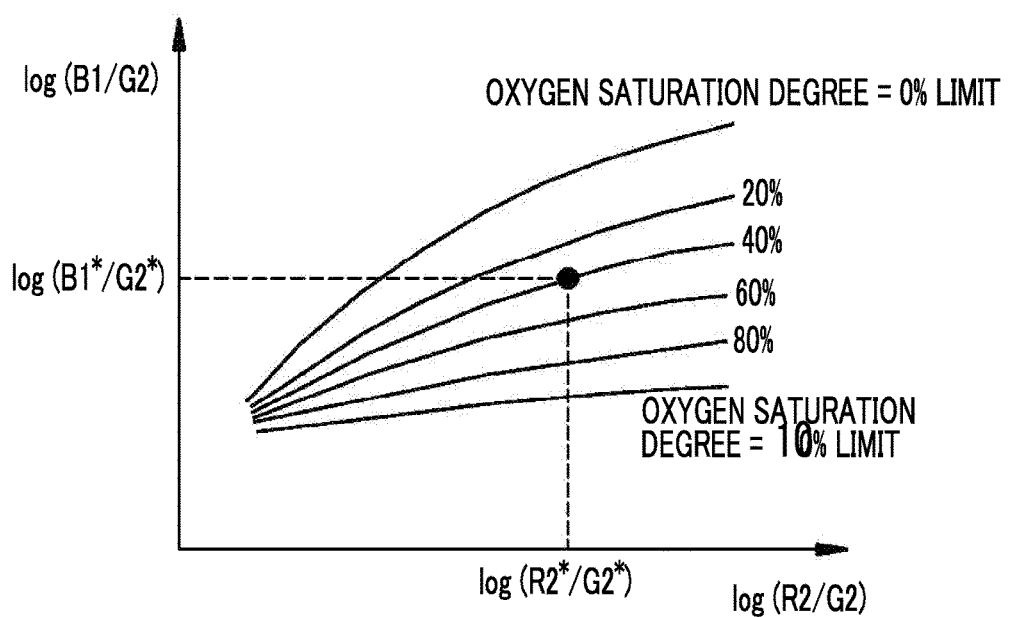
FIG. 10 is an explanatory view illustrating a method for calculating the oxygen saturation degree.

The oxygen saturation degree calculation unit 74 refers to a correlation stored in the correlation storage unit 72, and calculates an oxygen saturation degree corresponding to the signal ratios B1/G2 and R2/G2 for each pixel. For example, as illustrated in FIG. 10, in a case where the correlation stored in the correlation storage unit 72 is referred to, an oxygen saturation degree corresponding to the signal ratios B1*/G2* and R2*/G2* of a specific pixel is "40%". Hence, the oxygen saturation degree calculation unit 74 calculates the oxygen saturation degree as "40%".

In addition, the signal ratio B1/G2, R2/G2 hardly become extremely large or extremely small. That is, the combination of the respective values of the signal ratios B1/G2 and R2/G2 is hardly distributed below the isogram 83 (refer to FIG. 8) of an upper limit that is an oxygen saturation degree of 100% or conversely, the combination is hardly distributed above the isogram 84 (refer to FIG. 8) of a lower limit that is an oxygen saturation degree of 0%. However, in a case where the combination is distributed below the isogram 83 of the upper limit, the oxygen saturation degree is 100%, and in a case where the combination is distributed above the isogram 84 of the lower limit, the oxygen saturation degree calculation unit 74 sets the oxygen saturation degree as 0%. Additionally, in a case where a point corresponding to the signal ratios B1/G2 and R2/G2 is not distributed between the isogram 83 of the upper limit and the isogram 84 of the lower limit, a display may be performed such that it can be seen that the reliability of the oxygen saturation degree in the pixel is low, and the oxygen saturation degree may not be calculated.

The image generation unit 76 creates an oxygen saturation degree image obtained by imaging the oxygen saturation degree, using the oxygen saturation degree calculated by the oxygen saturation degree calculation unit 74. Specifically, the image generation unit 76 acquires the B2 image signal, the G2 image signal, and the R2 image signal, and multiplies these image signals by a gain according to the oxygen saturation degree for each pixel. Then, RGB image data is created using the B2 image signal, the G2 image signal, and the R2 image signal to which the gain is multiplied. For example, the image generation unit 76 multiplies all of the B2 image signal, the G2 image signal, and the R2 image signal by the same gain "1" in pixels with an oxygen saturation degree of 60% or more. In contrast, in pixels with an oxygen saturation degree of less than 60%, the B2 image signal is multiplied by a gain of less than "1", and the G2 image signal and the R2 image signal are multiplied by a gain of "1" or more. RGB image data created using the B2 image signal, the G2 image signal, and the R2 image signal after this gain processing is the oxygen saturation degree image.

In the oxygen saturation degree image generated by the image generation unit 76, a high-oxygen region (a region where the oxygen saturation degree is 60 to 100%) is expressed in the same color as a normal observation image. On the other hand, a low-oxygen region where the oxygen saturation degree is less than a specific value (a region where the oxygen saturation degree is 0 to 60%) is expressed in a color (pseudo-color) different from the normal observation image.

In addition, in the present embodiment, the image generation unit 76 multiplies the low-oxygen region to a gain for pseudo-coloring. However, the gain according to the oxygen saturation degree may also be multiplied to the high-oxygen region, and the overall oxygen saturation degree image may be pseudo-colored. Additionally, although the low-oxygen region and the high-oxygen region are divided at an oxygen saturation degree of 60%, this boundary is also arbitrary.

Figure 11:
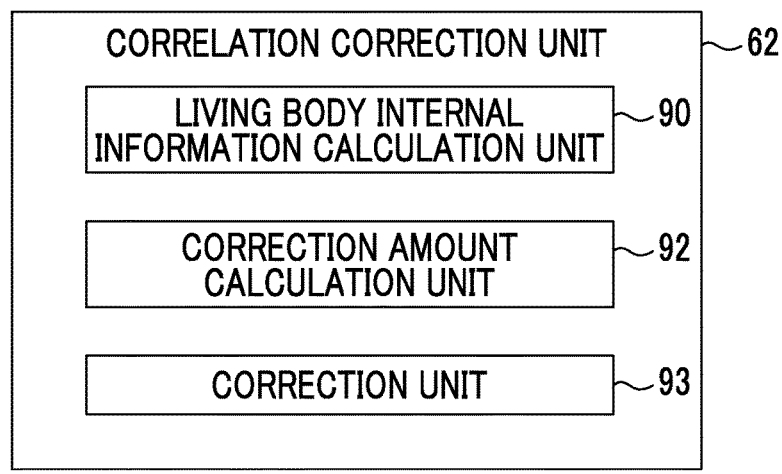
FIG. 11 is a block diagram illustrating the functions of a correlation correction unit.

As illustrated in FIG. 11, the correlation correction unit 62 includes a living body internal information calculation unit 90, a correction amount calculation unit 92, and a correction unit 93. The living body internal information calculation unit 90 has information on the yellow pigment in the living body, from the input Bp image signal, Bq image signal, Gr image signal, and Rs image signal, and calculates living body internal information that is not influenced by the oxygen saturation degree. Specifically, a signal ratio Bp/Gr (corresponding to a "first signal ratio" of the invention) of the Bp image signal and the Gr image signal is calculated for each pixel, a signal ratio Bq/Gr (corresponding to a "second signal ratio" of the invention) of the Bq image signal and the Gr image signal is calculated for each pixel, and a signal ratio Rs/Gr (corresponding to a "third signal ratio" of the invention) of the Rs image signal and the Gr image signal is calculated for each pixel.

Figure 12:
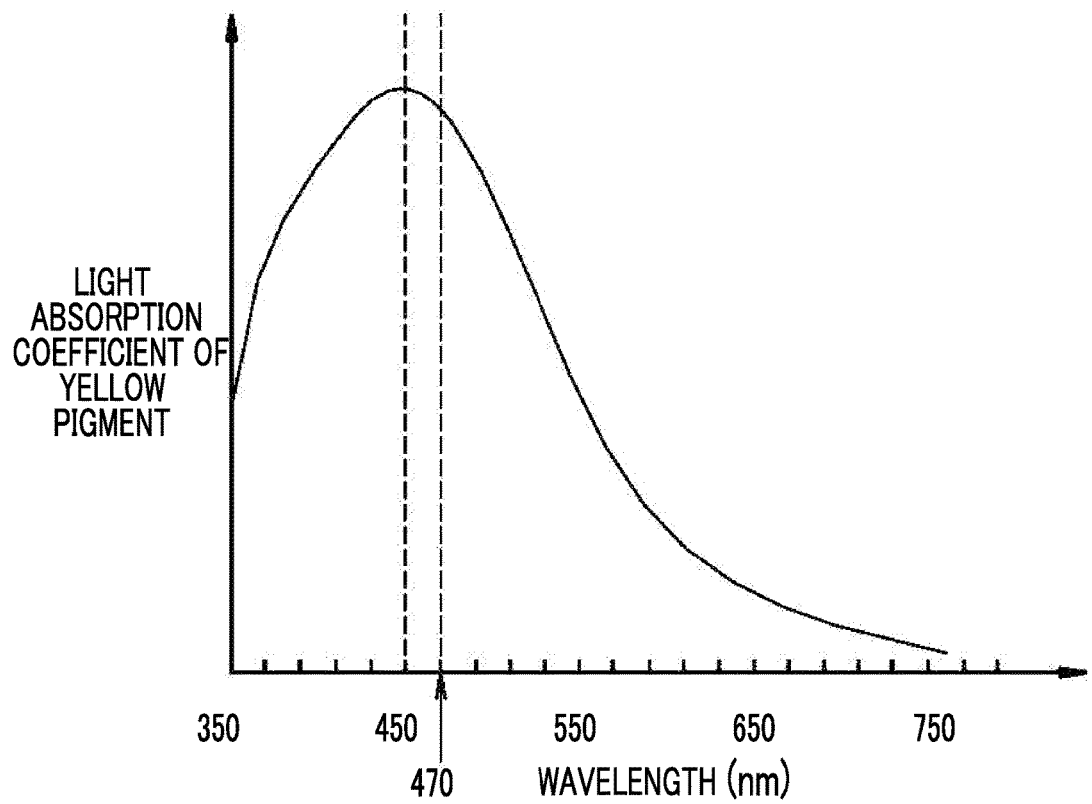
FIG. 12 is a graph illustrating the light absorption coefficient of a yellow pigment.

Here, Bp of the signal ratio Bp/Gr is an image signal corresponding to the first blue light BS. The wavelength band of 450±10 nm of the first blue light BS, as illustrated in FIG. 9, belongs to a blue band where the light absorption coefficient of hemoglobin is relatively high, and has an isosbestic wavelength where the light absorption coefficients of the oxygenated hemoglobin and the reduced hemoglobin are the same. Additionally, the wavelength band of 450±10 nm of the first blue light BS, as illustrated in FIG. 12, is a wavelength band where the light absorption amount easily varies according to the density of the yellow pigment because the wavelength band has an absorption peak wavelength where the light absorption coefficient of the yellow pigment is highest. Hence, in the signal ratio Bp/Gr, signal values do not vary depending on the oxygen saturation degree, but the signal values vary depending on the density of the yellow pigment or the amount of blood. In addition, since the wavelength band of 540±20 nm of the green light included in the Gr image signal is a wavelength band where the light absorption amount easily varies depending on the amount of blood, as described above.

Bq of the signal ratio Bq/Gr is an image signal corresponding to the second blue light BL. Since the wavelength band of 470±10 nm of the second blue light BL, as described above, belongs to a blue band where the light absorption coefficient of hemoglobin is relatively high, and has different absorption wavelengths where the light absorption coefficients of the oxygenated hemoglobin and the reduced hemoglobin are different from each other (refer to FIG. 9), the wavelength band is a wavelength band where the light absorption amount easily varies depending on the oxygen saturation degree of hemoglobin. Additionally, the center wavelength of 470 nm of the second blue light BL has a larger light absorption coefficient than the other wavelength bands (refer to FIG. 12), though the light absorption coefficient becomes slightly low from the absorption peak wavelength of the yellow pigment. Hence, in the signal ratio Bq/Gr, signal values vary depending on the oxygen saturation degree, the density of the yellow pigment, and the amount of blood. In contrast, in the signal ratio Rs/Gr, signal values hardly vary depending on the oxygen saturation degree and the density of the yellow pigment, but the signal values vary depending on the amount of blood.

The living body internal information calculation unit 90 adjusts $\phi$ such that a second calculated value obtained by the calculation for correction based on the following Equation A becomes constant even if the oxygen saturation degree varies. Information consisting of the second calculated value after this $\phi$ adjustment and the signal ratio Rs/Gr is defined as the living body internal information. This living body internal information is information that varies according to the density of the yellow pigment, and is information that does not vary depending on the oxygen saturation degree.

Second calculated value=Signal ratio $Bp/Gr \times \cos \phi$ –Signal ratio $Bq/Gr \times \sin \phi$. (Equation A)

The correction amount calculation unit 92 calculates correction amount $\Delta D$ from predetermined reference information, and the living body internal information calculated by the living body internal information calculation unit 90. The reference information is set as information that is obtained in a state where there is no yellow pigment, and does not vary depending on the oxygen saturation degree. Specifically, the reference information is obtained by adjusting $\phi$ such that the second calculated value based on the following Equation A becomes constant even if the oxygen saturation degree varies in a state where the influence caused by the yellow pigment is eliminated (namely, a state with no yellow pigment). The calculation of the correction amount $\Delta D$ using the correction amount calculation unit 92 will be described below using a second feature space (corresponding to "a feature space for correction" of the invention) in which a vertical axis is formed by the second calculated value (=signal ratio $Bp/Gr \times \cos \phi$–signal ratio $Bq/Gr \times \sin \phi$) based on Equation (A) and a horizontal axis is formed by Log(Rs/Gr). In addition, in the second feature space, the vertical axis corresponds to a "first axis" of the invention, and the horizontal axis corresponds to a "second axis" of the invention.

Figure 13:
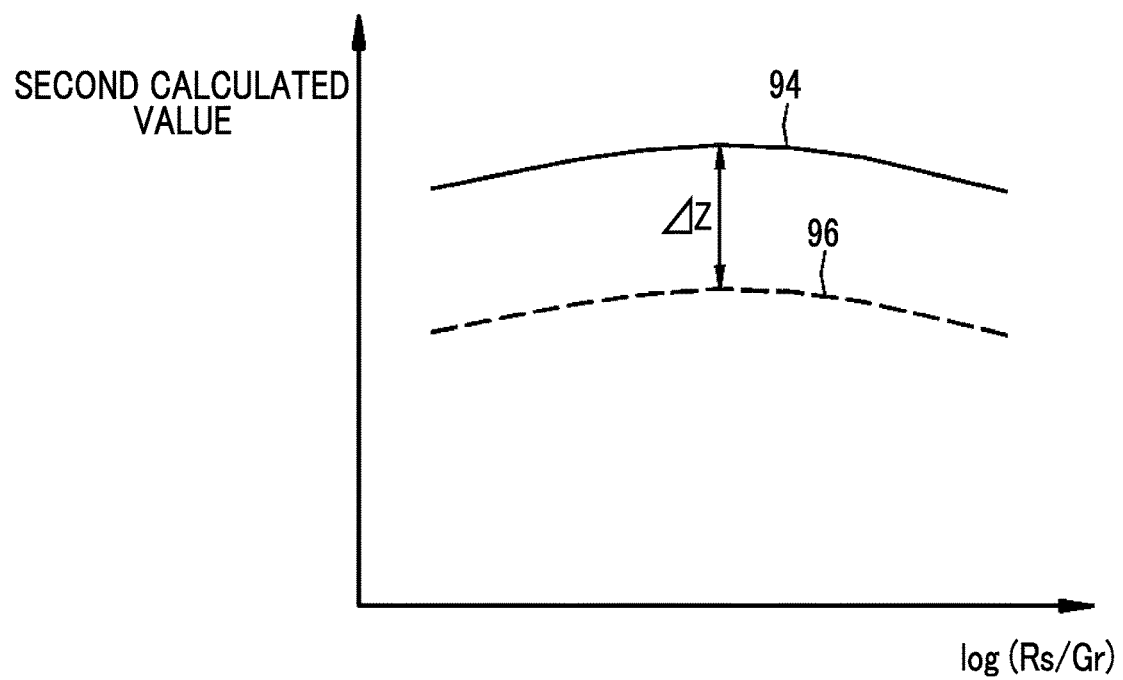
FIG. 13 is a graph illustrating the positions of a reference line and an actual measurement line in a second feature space in which a vertical axis represents second calculated value and a horizontal axis represents Log(Rs/Gr).

In a case where the reference information and the living body internal information are expressed on the second feature space, as illustrated in FIG. 13, a reference line 94 showing the distribution of the reference information with no influence of the yellow pigment, and an actual measurement line 96 on which the living body internal information influenced by the yellow pigment is distributed are formed substantially in a horizontal axis direction, respectively. The actual measurement line 96 is an equal density line on which the density of the yellow pigment is the same. Additionally, in the second feature space, the reference line 94 is located above the actual measurement line 96. Additionally, in the second feature space, as the influence of the yellow pigment becomes larger, the actual measurement line 96 is located to be lower and the difference between the reference line 94 and the actual measurement line 96 becomes larger.

In the correction amount calculation unit 92, a difference $\Delta Z$ between the reference line 94 and the actual measurement line 96 is calculated. The correction amount $\Delta D$ is calculated by multiplying this calculated difference $\Delta Z$ by a coefficient $\alpha$ (Correction amount $\Delta D$=Difference $\Delta Z \times$ Coefficient $\alpha$). In addition, the correction amount $\Delta D$ may be calculated by performing conversion processing, in which matrix processing and a one-dimensional look up table (1D-LUT) are combined, on the Bp image signal, the Bq image signal, the Gr image signal, and the Rs image signal.

The correction unit 93 corrects the correlation stored in the correlation storage unit 72 on the basis of the correction amount $\Delta D$ calculated using the correction amount calculation unit 92. Specifically, in the first feature space, the correction amount $\Delta D$ is added to the value of Log(B1/G2) of the vertical axis. Accordingly, in the first feature space, an isogram obtained by connecting portions with the same oxygen saturation degree moves in a vertical axis Log(B1/G2) direction. By calculating the oxygen saturation degree using a correlation after this correction, the oxygen saturation degree can be accurately calculated even in a situation where the influence of the yellow pigment is present on the observation target in addition to a case where there are various sites or patients are different.

Figure 14:
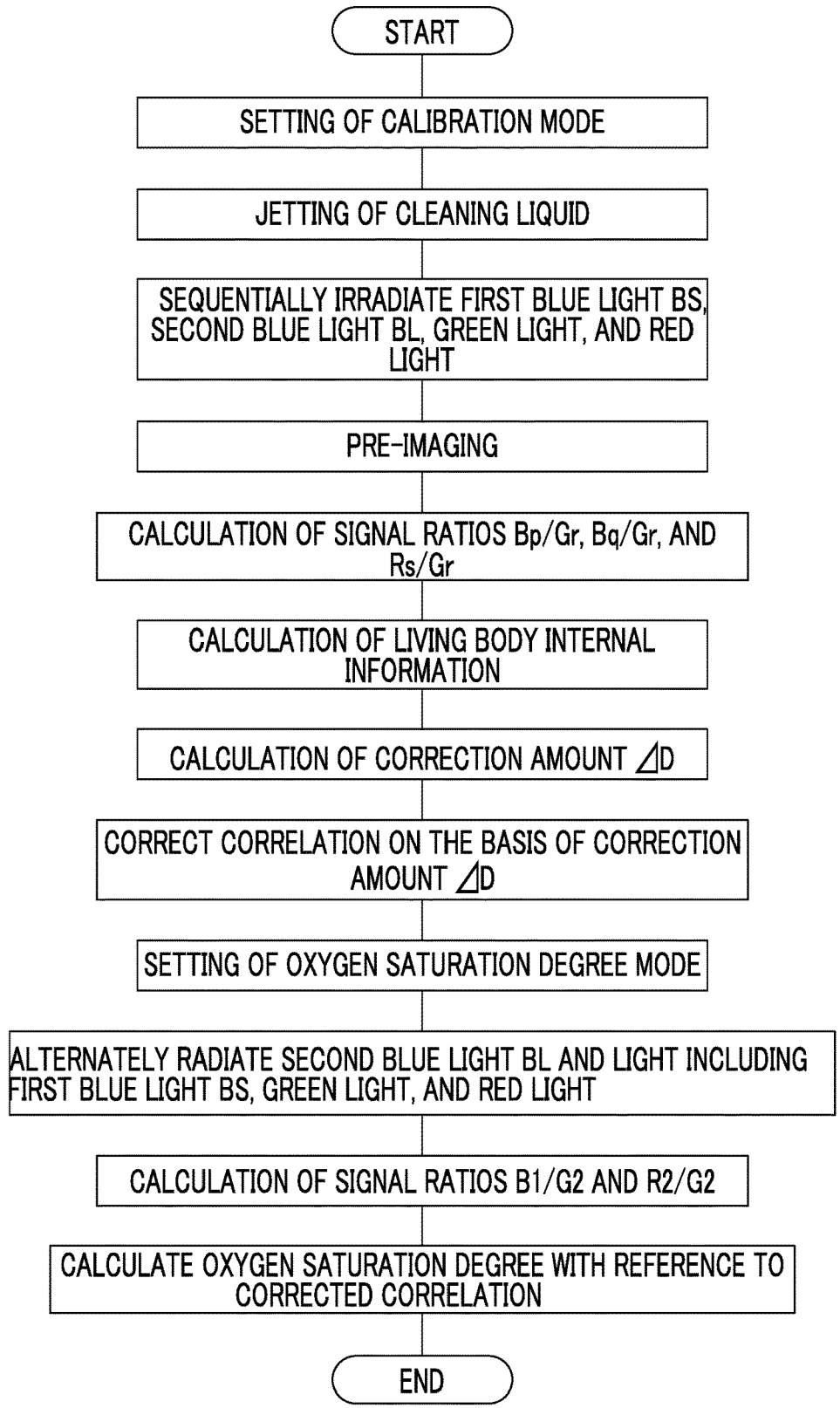
FIG. 14 is a flowchart illustrating a series of flow in the first embodiment of the invention.

Next, a series of flow of the present embodiment of the invention will be described along a flowchart in FIG. 14. A mode switchover SW 12f is operated to set the calibration mode. If the calibration mode is set, a cleaning liquid is jetted from the distal end part 12d of the endoscope 12 to the observation target. Accordingly, most of the yellow pigment or the like on the observation target is removed. Additionally, the first blue light BS, the second blue light BL, the green light and the red light R are sequentially emitted by sequentially turning on the respective LEDs 20a to 20d. The four-color lights are radiated to the observation target, and are imaged by the imaging sensor 44. An image of the observation target is displayed on the monitor 18 on the basis of the image signals output from the imaging sensor.

Then, pre-imaging of the cleaned observation target is performed by the operation of the still image acquisition instruction unit 12g to acquire image signals (this corresponds to a "first image signal acquisition step" of the invention). The Bp image signal, the Bq image signal, the Gr image signal, and the Rs image signal among the image signals obtained by this pre-imaging are transmitted to the correlation correction unit 62. In the correlation correction unit 62, the living body internal information calculation unit 90 calculates the signal ratio Bp/Gr of the Bp image signal and the Gr image signal for each pixel, calculates the signal ratio Bq/Gr of the Bq image signal and the Gr image signal for each pixel, and calculates the signal ratio Rs/Gr of the Rs image signal and the Gr image signal for each pixel. Then, the living body internal information is calculated on the basis of these three signal ratios Bp/Gr, Bq/Gr, and Rs/Gr.

The correction amount calculation unit 92 calculates correction amount $\Delta D$ from predetermined reference information, and the living body internal information calculated by the living body internal information calculation unit 90. The correction unit 93 corrects the correlation stored in the correlation storage unit 72 on the basis of the calculated correction amount $\Delta D$. Accordingly, the calibration mode is completed. Here, "the processing from the calculation of the correction amount $\Delta D$ to the correction of the correlation" corresponds a "correlation correction step" of the invention. In addition, in the calibration mode, the simultaneous emission of the first blue light BS, the green light and the red light R may be performed so as to display the normal image before the pre-imaging performed by the operation of the still image acquisition instruction unit 12g.

If the calibration mode is completed, automatic switching to the oxygen saturation degree mode is performed. If switching to the oxygen saturation degree mode is performed, light including the first blue light BS, the second blue light BL, the green light G, and the red light R are alternately emitted, and imaging is performed for each light emission. The B1 image signal, the G2 image signal, and the R2 image signal used for the calculation of the oxygen saturation degree are obtained by this imaging (this corresponds to a "second image signal acquisition step" of the invention). Next, the signal ratio B1/G2 of the B1 image signal and the G2 image signal and the signal ratio R2/G2 of the R2 image signal and the G2 image signal are calculated. Then, an oxygen saturation degree corresponding to the signal ratios B1/G2 and R2/G2 are calculated by referring to the correlation corrected by the correction unit 93 (this corresponds to an "oxygen saturation degree calculation step" of the invention).

Second Embodiment

In a second embodiment, the observation target is illuminated using a broadband light source, such as a xenon lamp, and a rotation filter instead of the four-color LEDs 20a to 20d illustrated in the first embodiment above. Additionally, the observation target is imaged by a monochrome imaging sensor instead of the color imaging sensor 44. The others are the same as those of the first embodiment.

Figure 15:
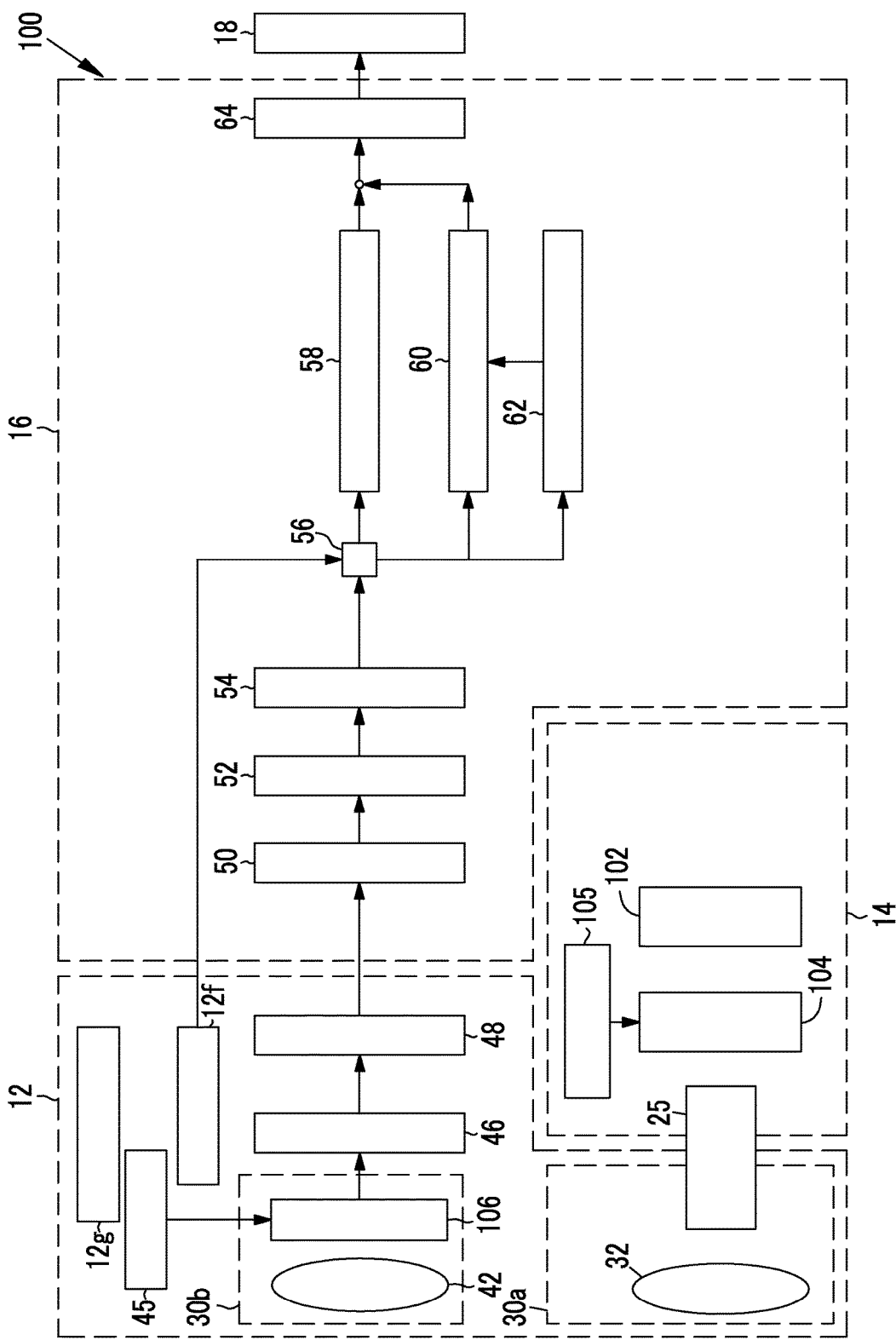
FIG. 15 is a block diagram illustrating the functions of an endoscopic system of a second embodiment.

As illustrated in FIG. 15, in an endoscopic system 100 of the second embodiment, in the light source device 14, a broadband light source 102, a rotation filter 104, and a filter switching unit 105 are provided instead of the four-color LEDs 20a to 20d. Additionally, the imaging optical system 30b is provided with a monochrome imaging sensor 106 that is not provided with a color filter instead of the color imaging sensor 44.

The broadband light source 102 is a xenon lamp, a white LED, or the like, and emits white light whose wavelength band ranges from blue to red. The rotation filter 104 includes an inner filter 108 provided inside and an outer filter 109 provided outside (refer to FIG. 16). The filter switching unit 105 moves the rotation filter 104 in a radial direction, inserts the inner filter 108 of the rotation filter 104 into an optical path for the white light when the normal mode is set by the mode switchover SW 12f, and inserts the outer filter 109 of the rotation filter 104 into the optical path of the white light when the oxygen saturation degree mode or the calibration mode is set.

Figure 16:
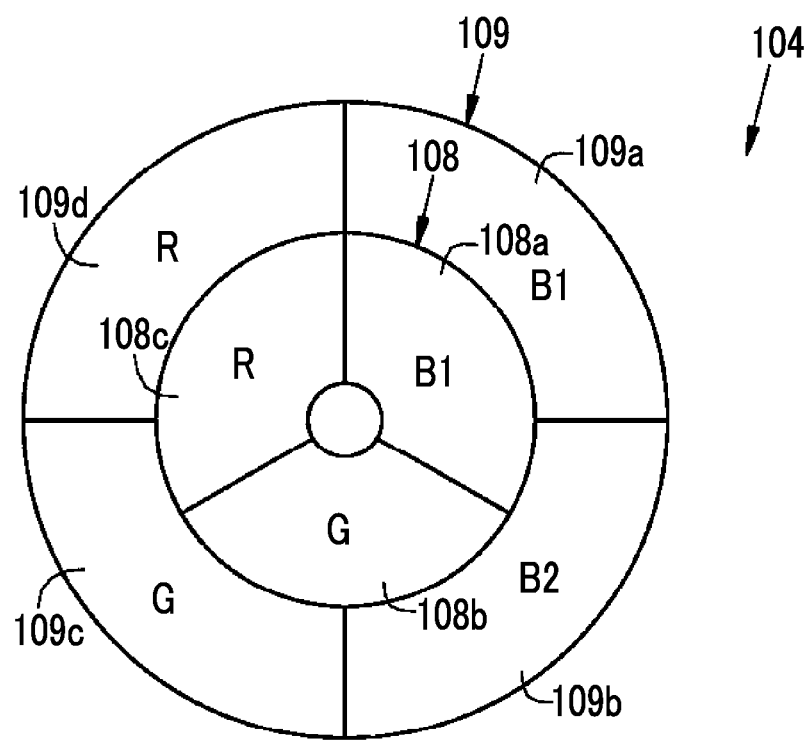
FIG. 16 is a plan view of a rotation filter.

As illustrated in FIG. 16, a B1 filter 108a that allows a first blue light BS of the white light to be transmitted therethrough, a G filter 108b that allows the green light G of the white light to be transmitted therethrough, and an R filter 108c that allows the red light R of the white light to be transmitted therethrough are provided in a circumferential direction at the inner filter 108. Hence, in the normal mode, the first blue light BS, the green light and the red light R are alternately radiated to the observation target by the rotation of the rotation filter 104.

A B1 filter 109a (corresponding to a "first filter" of the invention) that allows the first blue light BS of the white light to be transmitted therethrough, a B2 filter 109b (corresponding to a "second filter" of the invention) that allows the second blue light BL of the white light to be transmitted therethrough, a G filter 109c (corresponding to a "third filter" of the invention) that allows the green light G of the white light to be transmitted therethrough, and an R filter 109d (corresponding to a "fourth filter" of the invention) that allows the red light R of the white light to be transmitted therethrough are provided in the circumferential direction at the outer filter 109. Hence, in the oxygen saturation degree mode or the calibration mode, the first blue light BS, the second blue light BL, the green light and the red light R are alternately radiated to the observation target as the rotation filter 104 rotates.

In the endoscopic system 100, in the normal mode, whenever the observation target is illuminated by the first blue light BS, the green light and the red light R, the observation target is imaged by the monochrome imaging sensor 106. Accordingly, the Bc image signal, the Gc image signal, and the Rc image signal are obtained. Then, a normal image is created by the same method as the first embodiment above on the basis of the three-color image signals.

On the other hand, in the oxygen saturation degree mode, whenever the observation target is illuminated by the first blue light BS, the second blue light BL, the green light and the red light R, the observation target is imaged by the monochrome imaging sensor 106. Accordingly, the B2 image signal, the B1 image signal and the G2 image signal, and the R2 image signal are obtained. An oxygen saturation degree image is created by the same method as the first embodiment on the basis of the four-color image signals. Additionally, in the calibration mode, the Bp image signal, the Bq image signal, the Gr image signal, and the Rs image signal are obtained. A correlation is corrected by the same method as the first embodiment on the basis of the four-color image signals.

In addition, in the above embodiment, the first blue light BS whose wavelength band is 450±10 nm is used in order to correct the correlation in the calibration mode. However, light in a wavelength band where the light absorption coefficients of the oxygenated hemoglobin and the reduced hemoglobin are the same and where the light absorption coefficient of the yellow pigment is larger compared to the other wavelength bands may be used. For example, green narrow-band light whose wavelength band is 500±10 nm may be used instead of the first blue light BS.

In the above-described embodiment, hardware structures of processing units, which execute various kinds of processing, such as the image signal acquisition unit 50, the noise reduction unit 54, the image processing switching unit 56, the normal image generation unit 58, the oxygen saturation degree image generation unit 60, the correlation correction unit 62, and the video signal generation unit 64 are various processors as illustrated below. Various processors include exclusive electric circuits, which are processors having circuit configurations exclusively designed to execute specific processing, such as a central processing unit (CPU) that is a general-purpose processor that executes software (programs) to function as various processing units, a programmable logic device (PLD) that is a processor capable of changing a circuit configuration after manufacture of a field programmable gate array (FPGA) or the like, and an application specific integrated circuit (ASIC).

One processing unit may be constituted of one of these various processors, or may be constituted of two or more same or different processors (for example, a plurality of the FPGAs or a combination of the CPU and the FPGA). Additionally, the plurality of processing units may be constituted of one processor. As an example in which the plurality of processing units are constituted of the one processor, firstly, as represented by a computer, such as a client or a server, there is a form in which one processor is constituted of a combination of one or more CPUs and software and this processor functions as a plurality of processing units. Secondly, as represented by a system-on-chip (SOC) or the like, there is a form in which a processor, which realizes functions of an overall system including a plurality of processing units with one integrated circuit (IC) chip, is used. In this way, the various processing units are configured by using one or more of the above various processors as the hardware structure(s).

Moreover, the hardware structures of these various processors are more specifically circuitries in which circuit elements, such as semiconductor elements, are combined together.

EXPLANATION OF REFERENCES

10: endoscopic system
12: endoscope
12a: insertion part
12b: operating part
12c: bending part
12d: distal end part
12e: angle knob
12f: mode switchover SW
12g: still image acquisition instruction unit
14: light source device
16: processor device
18: monitor
19: console
20: light source
20a: BS-LED
20b: BL-LED
20c: G-LED
20d: R-LED
21: light source control unit
23: optical path coupling unit
25: light guide
30a: illumination optical system
30b: imaging optical system
32: illumination lens
42: objective lens
44: imaging sensor
45: imaging control unit
46: CDS/AGC circuit
48: A/D converter
50: image signal acquisition unit
52: DSP
54: noise reduction unit
56: image processing switching unit
58: normal image generation unit
60: oxygen saturation degree image generation unit
62: correlation correction unit 64: video signal generation unit
70: signal ratio calculation unit
72: correlation storage unit
74: oxygen saturation degree calculation unit
76: image generation unit
80: graph
81: graph
83: isogram
84: isogram
90: living body internal information calculation unit
92: correction amount calculation unit
93: correction unit
94: reference line
96: actual measurement line
102: broadband light source
104: rotation filter
105: filter switching unit
106: imaging sensor
108: inner filter
108a: B1 filter
108b: G filter
108c: R filter
109: outer filter
109a: B1 filter
109b: B2 filter
109c: G filter
109d: R filter

What is claimed is:

1. A processor device comprising:
a processor configured to acquire a first image signal corresponding to a first wavelength band whose light absorption amount varies according to a density of a pigment other than hemoglobin among pigments included in an observation target, a second image signal corresponding to a second wavelength band whose light absorption amount varies according to an oxygen saturation degree of the hemoglobin included in the observation target, a third image signal corresponding to a third wavelength band that has a wavelength longer than the first wavelength band and the second wavelength band and whose light absorption amount varies according to an amount of blood, and a fourth image signal corresponding to a fourth wavelength band that has a wavelength longer than the third wavelength band; and
a memory that stores a correlation between a first calculated value obtained by a specific calculation based on the second image signal, the third image signal, and the fourth image signal, and the oxygen saturation degree,
wherein the processor is further configured to:
calculate a correction amount of the correlation on the basis of the first image signal, the second image signal, the third image signal, and the fourth image signal, and correct the correlation on the basis of the correction amount,
calculate information in a living body of the observation target on the basis of a first signal ratio between the first image signal and the third image signal, a second signal ratio between the second image signal and the third image signal, and a third signal ratio between the fourth image signal and the third image signal, and
calculate the correction amount on the basis of predetermined reference information and the living body internal information, and correct the correlation on the basis of the correction amount,
calculate the oxygen saturation degree with reference to the corrected correlation, and
create an oxygen saturation degree image based on the calculated oxygen saturation degree.

2. The processor device according to claim 1,
wherein, in a feature space for correction having a second calculated value obtained by calculation for correction based on the first signal ratio and the second signal ratio as a first axis and having the third signal ratio as a second axis, the reference information is distributed on a reference line, and the living body internal information is distributed on an actual measurement line at a position different from the reference line, and
wherein the correction amount is calculated on the basis of a difference between the reference line and the actual measurement line.

3. The processor device according to claim 2,
wherein the first wavelength band has an isosbestic wavelength where light absorption coefficient of an oxygenated hemoglobin and a reduced hemoglobin are the same.

4. The processor device according to claim 2,
wherein the pigment other than hemoglobin is yellow pigment.

5. The processor device according to claim 1,
wherein the reference information is information obtained in a case where there is no influence of the pigment other than hemoglobin, and is information that does not vary depending on the oxygen saturation degree, and
wherein the living body internal information is information that varies according to the density of the pigment other than hemoglobin, and is information that is constant with respect to the oxygen saturation degree.

6. The processor device according to claim 5,
wherein the first wavelength band has an isosbestic wavelength where light absorption coefficient of an oxygenated hemoglobin and a reduced hemoglobin are the same.

7. The processor device according to claim 5,
wherein the pigment other than hemoglobin is yellow pigment.

8. The processor device according to claim 2,
wherein the reference information is information obtained in a case where there is no influence of the pigment other than hemoglobin, and is information that does not vary depending on the oxygen saturation degree, and
wherein the living body internal information is information that varies according to the density of the pigment other than hemoglobin, and is information that is constant with respect to the oxygen saturation degree.

9. The processor device according to claim 8,
wherein the first wavelength band has an isosbestic wavelength where light absorption coefficient of an oxygenated hemoglobin and a reduced hemoglobin are the same.

10. The processor device according to claim 8,
wherein the pigment other than hemoglobin is yellow pigment.

11. The processor device according to claim 1,
wherein the first wavelength band has an isosbestic wavelength where light absorption coefficients of an oxygenated hemoglobin and a reduced hemoglobin are the same.

12. The processor device according to claim 1,
wherein the pigment other than hemoglobin is yellow pigment.

13. The processor device according to claim 1,
wherein the first wavelength band is 450±10 nm, the second wavelength band is 470±10 nm, the third wavelength band is 540±20 nm, and the fourth wavelength band is 640±20 nm.

14. The processor device according to claim 1,
wherein the processor is configured to acquire the first image signal, the second image signal, the third image signal, and the fourth image signal in a calibration mode where the correlation is corrected, and acquire the second image signal, the third image signal, and the fourth image signal in an oxygen saturation degree mode where the oxygen saturation degree is calculated,
wherein calculation of the correction amount and correction of the correlation are performed in the processor on the basis of the first image signal, the second image signal, the third image signal, and the fourth image signal that are acquired in the calibration mode, and
wherein the oxygen saturation degree is calculated in the processor with reference to a corrected correlation on the basis of the second image signal, the third image signal, and the fourth image signal that are acquired in the oxygen saturation degree mode.

15. An endoscopic system comprising:
the processor device according to claim 1; and
a light source device having a first semiconductor light source that emits light in the first wavelength band, a second semiconductor light source that emits light in the second wavelength band, a third semiconductor light source that emits light in the third wavelength band, and a fourth semiconductor light source that emits light in the fourth wavelength band.

16. An endoscopic system comprising:
the processor device according to claim 1; and
a light source device having a broadband light source that emits white light and a rotation filter provided with a first filter that allows light in the first wavelength band of the white light to be transmitted therethrough, a second filter that allows light in the second wavelength band of the white light to be transmitted therethrough, a third filter that allows light of the third wavelength band of the white light to be transmitted therethrough, and a fourth filter that allows light of the fourth wavelength band of the white light to be transmitted therethrough.

17. A method for operating a processor device comprising:
a first image signal acquisition step of a processor acquiring a first image signal corresponding to a first wavelength band whose light absorption amount varies according to a density of a pigment other than hemoglobin among pigments included in an observation target, a second image signal corresponding to a second wavelength band whose light absorption amount varies according to an oxygen saturation degree of the hemoglobin included in the observation target, a third image signal corresponding to the third wavelength band that has a wavelength longer than the first wavelength band and the second wavelength band and whose light absorption amount varies according to an amount of blood, and a fourth image signal corresponding to a fourth wavelength band that has a wavelength longer than the third wavelength band;
a correlation correction step of the processor calculating a correction amount of a correlation between a first calculated value obtained by a specific calculation based on the second image signal, the third image signal, and the fourth image signal, and the oxygen saturation degree on the basis of the first image signal, the second image signal, the third image signal, and the fourth image signal, and to correct the correlation on the basis of the correction amount,
wherein the correlation correction step includes a living body internal information calculation step of the processor calculating information in a living body of the observation target on the basis of a first signal ratio between the first image signal and the third image signal, a second signal ratio between the second image signal and the third image signal, and a third signal ratio between the fourth image signal and the third image signal, a correction amount calculation step of the processor calculating the correction amount on the basis of predetermined reference information and the living body internal information, and a correction step of the processor correcting the correlation on the basis of the correction amount,
a calculation step of the processor calculating the oxygen saturation degree with reference to the corrected correlation, and
a creation step of the processor creating an oxygen saturation degree image based on the calculated oxygen saturation degree.

18. The method for operating a processor device according to claim 17 in which, in the first image signal acquisition step, the processor acquires the first image signal, the second image signal, the third image signal, and the fourth image signal in a calibration mode where the correlation is corrected, and, in the correlation correction step, the processor performs calculation of the correction amount and correction of the correlation on the basis of the first image signal, the second image signal, the third image signal, and the fourth image signal that are acquired in the calibration mode,
the method further comprising:
a second image signal acquisition step of the processor acquiring the second image signal, the third image signal, and the fourth image signal in an oxygen saturation degree mode where the oxygen saturation degree is calculated; and
an oxygen saturation degree calculation step of the processor calculating the oxygen saturation degree with reference to a corrected correlation on the basis of the second image signal, the third image signal, and the fourth image signal that are acquired in the oxygen saturation degree mode.

19. A method for operating an endoscopic system comprising:
a light emission step of causing a light source device to sequentially emit light in a first wavelength band whose light absorption amount varies according to a density of a pigment other than hemoglobin among pigments included in an observation target, light in a second wavelength band whose light absorption amount varies according to an oxygen saturation degree of the hemoglobin included in the observation target, light in a third wavelength band that has a wavelength longer than the first wavelength band and the second wavelength band and whose light absorption amount varies according to an amount of blood, and light in a fourth wavelength band that has a wavelength longer than the third wavelength band,
a first image signal acquisition step of the processor acquiring a first image signal corresponding to the first wavelength band, a second image signal corresponding to the second wavelength band, a third image signal corresponding to the third wavelength band, and a fourth image signal corresponding to the fourth wavelength band;

a correlation correction step of the processor calculating a correction amount of a correlation between a first calculated value obtained by a specific calculation based on the second image signal, the third image signal, and the fourth image signal, and the oxygen saturation degree on the basis of the first image signal, the second image signal, the third image signal, and the fourth image signal, and to correct the correlation on the basis of the correction amount, wherein the correlation correction step includes a living body internal information calculation step of the processor calculating information in a living body of the observation target on the basis of a first signal ratio between the first image signal and the third image signal, a second signal ratio between the second image signal and the third image signal, and a third signal ratio between the fourth image signal and the third image signal, a correction amount calculation step of the processor calculating the correction amount on the basis of predetermined reference information and the living body internal information, and a correction step of the processor correcting the correlation on the basis of the correction amount, a calculation step of the processor calculating the oxygen saturation degree with reference to the corrected correlation, and a creation step of the processor creating an oxygen saturation degree image based on the calculated oxygen saturation degree.

20. The method for operating an endoscopic system according to claim 19 in which, in the first image signal acquisition step, the processor acquires the first image signal, the second image signal, the third image signal, and the fourth image signal in a calibration mode where the correlation is corrected, and in the correlation correction step, the processor performs calculation of the correction amount and correction of the correlation on the basis of the first image signal, the second image signal, the third image signal, and the fourth image signal that are acquired in the calibration mode, the method further comprising:

a second image signal acquisition step of the processor acquiring the second image signal, the third image signal, and the fourth image signal in an oxygen saturation degree mode where the oxygen saturation degree is calculated; and an oxygen saturation degree calculation step of the processor calculating the oxygen saturation degree with reference to a corrected correlation on the basis of the second image signal, the third image signal, and the fourth image signal that are acquired in the oxygen saturation degree mode.

* * * * *